United States Patent [19]
Tsuji et al.

[11] Patent Number: 5,202,117
[45] Date of Patent: Apr. 13, 1993

[54] METHOD OF TREATING THROMBI WITH G-CSF

[76] Inventors: Koichiro Tsuji, 6598, Toyota, Suwa-shi, Nagano-ken; Masayoshi Ono, 1369-7, Yamaguchi, Tokoroazawa-shi, Saitama-ken, both of Japan

[21] Appl. No.: 396,949

[22] Filed: Aug. 22, 1989

[30] Foreign Application Priority Data

Aug. 24, 1988 [JP] Japan .................. 63-210376

[51] Int. Cl.$^5$ .............................. A61K 37/02
[52] U.S. Cl. ...................... 424/85.1; 514/2; 514/12; 514/8; 514/21
[58] Field of Search .......... 424/85.1; 514/2, 12, 514/8, 21

[56] References Cited

U.S. PATENT DOCUMENTS 4,766,075  8/1988  Goeddel et al. .......... 435/240.2
5,120,534  6/1992  Hirai et al. ............. 424/85.1
5,126,325  6/1992  Kishimoto .............. 514/12

FOREIGN PATENT DOCUMENTS 0169566  1/1986  European Pat. Off. .

OTHER PUBLICATIONS

Morsteyn et al., *J. Clin. Cencalopy* 1989, vol. 7(10), pp. 1554–62.
Tanikawa et al., *Exp. Hematol.* 17 1989, pp. 883–88.
Kojima et al., *J. Cell Physiol.* 138(1) 1989, pp. 192–96 (abst. only).
Verstraete et al., Blood 67(6) 1986, pp. 1529–41.
Cohen et al., *PNAS* 84, 1987 pp. 2484–28.
H. Hagiwara et al., (1984) Thrombosis Res. 33: 363–370.
M. Shimonaka et al., (1984) Thrombosis Res. 36: 217–222.
Y. Inada et al., (1985) Biochem. Biophys. Res. Commun. 130: 182–187.
S. Kojima et al. (1986) Biomedical Res. 7:155–159.

Primary Examiner—Garnette D. Draper

[57] ABSTRACT

A thrombus control agent comprising a human granulocyte colony stimulating factor (human G-CSF) as an active ingredient and a pharmaceutically acceptable carrier, a method of treating thrombi by administering the thrombus control agent to a patient bearing thrombi formed in the arterial and venous vessels, and use of human G-CSF for preparing the thrombus control agent are disclosed.

The inventors found that human G-CSF is useful for treating thrombi and developed the use of human G-CSF for this purpose although nobody has clearly reported this type of pharmacological activity of human G-CSF.

17 Claims, 4 Drawing Sheets

Fig. 3
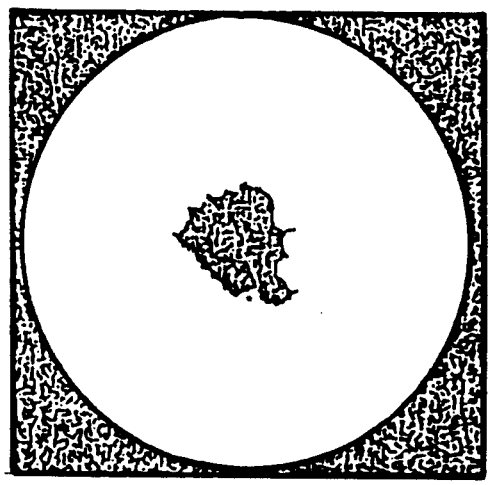 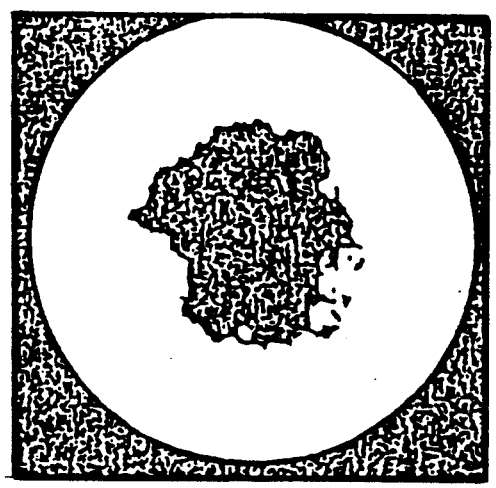
CONTROL GROUP
FIGURE 3(a)
TREATED GROUP
FIGURE 3(b)

METHOD OF TREATING THROMBI WITH G-CSF

FIELD OF THE INVENTION

The present invention relates to a thrombus control agent containing a human granulocyte colony stimulating factor (hereinafter abbreviated as "human G-CSF") as an active ingredient.

PRIOR ART

The present invention aims at treating arterial and venous thrombi by utilizing human G-CSF which is one of the humoral factors that enhance the hematopoietic capability of the human body, in particular, the fission, proliferation and maturation of neutrophiles. None of the scholarly reports published to date have disclosures that have direct bearing to the use of human G-CSF as a thrombus control agent.

Human G-CSF has been known as a humoral hematopoietic factor that acts on precursor cells of granulocytes in in vitro experimental systems to promote their growth and differentiation into granulocytes [see, for example, Metcalf et al., Exp. Hematol., 1, 185 (1973)]. However, because of the extreme difficulty so far encountered in obtaining it, studies on the utility or effectiveness of human G-CSF as a medicine have not been fully conducted and it has been entirely unknown that human G-CSF has the potential to be used in the treatment of thrombi, which is the principal object of the present invention.

Heparin and sigmarol in various dosage forms have conventionally been used as thrombus control drugs that delay coagulation of blood but a need has also existed for the development of drugs that lyse fibrin clots. Recently, large-scale production of urokinase and a plasminogen activator (PA) which are capable of activating the fibrinolytic system has been established and these substances have come to be used as thrombus control agents.

At the same time, the recent advances in technology, in particular, genetic engineering have enabled the development of a process by which a pure and homogeneous human G-CSF can be produced in large quantities (see Japanese Patent Public Disclosure Nos. 61-227526, 62-236497 and 62-236488).

Based on this state of the art, the present inventors undertook studies on the possible effects of human G-CSF on vascular endothelial cells which produce PA capable of activating the fibrinolytic system. As a result, the present inventors have found that human G-CSF enhances the production of PA which is capable of activating the fibrinolytic system and that therefore it can be used as a thrombus control agent that has high efficacy and which yet causes limited side effects.

With a view to attaining the objective described above, the present inventors conducted intensive studies using mammalian endothelial cells. In the studies conducted on bovine carotid arterial endothelial cells and Rhesus monkey, the following facts were established:

(1) Bovine carotid arterial endothelial cells (hereinafter referred to simply as "endothelial cells") preincubated in the presence of human G-CSF synthesized and secreted about five times as mush PA as when they were preincubated in the absence of human G-CSF;

(2) The PA production peaked when G-CSF was added in a concentration of about 50 ng/ml, which is substantially equal to an optimum concentration for the target cells in the hematopoietic system;

(3) As regards the promotion of PA synthesis and secretion by endothelial cells that were preincubated in the presence of human G-CSF, a significant correlation exists between the concentration of G-CSF addition and the period of preincubation.

(4) When fibrin gel was formed in a Petri dish and vascular endothelial cells were cultivated on the gel, PA was secreted in proportion as the cells grew in the presence of G-CSF and the plasminogen in the liquid culture was converted to plasmin, which lysed the fibrin gel; and (5) When human G-CSF was administered continuously to Rhesus monkey which is akin to human and an analysis made on a thromboelastogram of the fresh blood taken after 2 weeks, the occurrence of fibrin lysis was observed immediately after blood coagulation, and this would probably be due to the activation of the fibrinolytic system.

SUMMARY OF THE INVENTION

These results suggest the possibility that human G-CSF acts on vascular endothelial cells and promotes their PA synthesis and secretion in such a way that the plasminogen present in large quantities in blood is converted to plasmin, with the resulting plasmin selectively lysing the fibrin clots in the blood. The present invention has been accomplished on the basis of this mechanism and provides a thrombus control agent containing human G-CSF as an active ingredient.

BRIEF DESCRIPTION OF THE DRAWINGS

FIGS. 3A and 3B shows the effect of human G-CSF on the promotion of the fibrinolytic activity of endothelial cells.

DETAILED DESCRIPTION OF THE INVENTION

Figure 1:
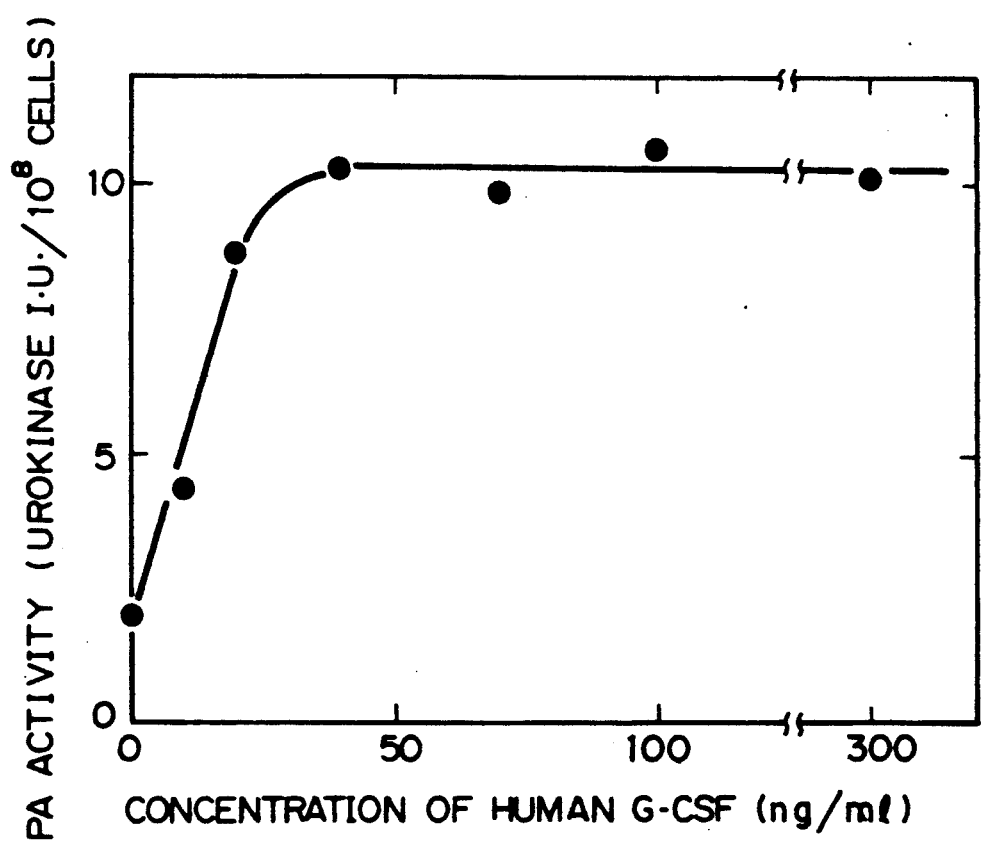
FIG. 1 is a graph showing the effect of human G-CSF on PA production by bovine vascular endothelial cells.

The human G-CSF which is used as the active ingredient of the thrombus control agent of the present invention may derive from any origin as long as it has high purity. For example, a human G-CSF may be prepared by extracting, separating and purifying from a human viable sample. A human G-CSF may be isolated from the supernatant of the culture of human G-CSF producing cells. Alternatively, a human G-CSF may be recovered from human G-CSF producing hybridomas produced by cell fusion. The recombinant gene technology may be utilized in such a way that a host such as E. coli or animal cells is subjected to transformation and a human G-CSF is produced is the transformant and isolated and purified therefrom. If desired, the amino acid sequence of native human G-CSF may be chemically modified to produce a desired human G-CSF.

Particularly preferred examples of the human G-CSF that may be used in the present invention are the following two that have high purity and that can be produced in large volume:

(1) human G-CSF having the following physicochemical properties:
i) molecular weight: about 19,000±1,000 as measured by electrophoresis through a sodium dodecylsulfatepolyacrylamide gel;
ii) isoelectric point: having at least one of the three isoelectric points, pI=5.5±0.1, pI=5.8±0.1, and pI=6.1±0.1;
iii) ultraviolet absorption: having a maximum absorption at 280 nm and a minimum absorption at 250 nm;
iv) amino acid sequence of the 21 residues from N-terminus;

H$_2$N—Thr—Pro—Leu—Gly—Pro—Ala—Ser—Ser—Leu—Pro—Gln—Ser—Phe—Leu—Leu—Lys—Cys—Leu—Glu—Gln—Val—

(2) human G-CSF containing either a polypeptide having the human granulocyte stimulating factor activity which is represented by all or part of the amino acid sequence shown below, or a glycoprotein having both said polypeptide and a sugar chain portion:

| (Met)$_n$ | Thr | Pro | Leu | Gly | Pro | Ala | Ser | Ser | Leu | Pro |
|---|---|---|---|---|---|---|---|---|---|---|
| Gln | Ser | Phe | Leu | Leu | Lys | Cys | Leu | Glu | Gln | Val |
| Arg | Lys | Ile | Gln | Gly | Asp | Gly | Ala | Ala | Leu | Gln |
| Glu | Lys | Leu | (Val | Ser | Glu)$_m$ | Cys | Ala | Thr | Tyr | Lys |
| Leu | Cys | His | Pro | Glu | Glu | Leu | Val | Leu | Leu | Gly |
| His | Ser | Leu | Gly | Ile | Pro | Trp | Ala | Pro | Leu | Ser |
| Ser | Cys | Pro | Ser | Gln | Ala | Leu | Gln | Leu | Ala | Gly |
| Cys | Leu | Ser | Gln | Leu | His | Ser | Gly | Leu | Phe | Leu |
| Tyr | Gln | Gly | Leu | Leu | Gln | Ala | Leu | Glu | Gly | Ile |
| Ser | Pro | Glu | Leu | Gly | Pro | Thr | Leu | Asp | Thr | Leu |
| Gln | Leu | Asp | Val | Ala | Asp | Phe | Ala | Thr | Thr | Ile |
| Trp | Gln | Gln | Met | Glu | Glu | Leu | Gly | Met | Ala | Pro |
| Ala | Leu | Gln | Pro | Thr | Gln | Gly | Ala | Met | Pro | Ala |
| Phe | Ala | Ser | Ala | Phe | Gln | Arg | Arg | Ala | Gly | Gly |
| Val | Leu | Val | Ala | Ser | His | Leu | Gln | Ser | Phe | Leu |
| Glu | Val | Ser | Tyr | Arg | Val | Leu | Arg | His | Leu | Ala |
| Gln | Pro | | | | | | | | | |

(provided that m is 0 or 1; and n is 0 or 1).

The human G-CSFs described above may be produced by the methods shown in the Referential Examples to be given below. Stated specifically, the human G-CSF under (1) can be produced by the method described in Referential Example 1, whereas the human G-CSF under (2) can be produced by the method described in Referential Example 2 (when m=0, the human G-CSF is conveniently designated −VSE, and when m=1, it is designated +VSE).

For details of the respective process conditions to be employed in these methods, see the specifications of commonly assigned Japanese Patent Public Disclosure Nos. 61-22752, 62-236497 and 62-236488.

Another method that can be employed consists of performing fusion of a G-CSF producing cell with a selfproliferating malignant tumor cell and cultivating the resulting hybridoma in the presence or absence of nitrogen.

All of the human G-CSFs that are obtained by the methods described above are included within the scope of the present invention.

The human G-CSF containing solution obtained may be stored frozen after aseptic filtration with a suitable filter medium such as a MILLIPORE filter following further purification and concentration that may be performed as required by any known techniques. Alternatively, the solution may be stored after being dehydrated by such means as freeze-drying or vacuum drying.

If desired, the human G-CSF may be used as an injection after being dissolved in distilled water or an appropriate buffer solution.

For the purpose of formulating the thrombus control agent of the present invention in a dosage form adapted for administration to humans or animals, one or more of the following additives may be incorporated: a pharmaceutical carrier and excipient, as well as a stabilizer and an antiadsorption agent.

The dose of the human G-CSF incorporated in the thrombus control agent of the present invention and the frequency of its administration may be determined in consideration of the severity of the disease to be treated. As guide figures, a formation containing human G-CSF in an amount of 0.1–1,000 μg, preferably 1–500 μg per adult may be administered 1–7 times a week.

It should however be noted that the present invention is by no means limited by the content of human G-CSF.

The present invention is hereunder described in greater detail with reference to referential examples (for the preparation of human G-CSF), experimental examples (for showing the pharmaceutical efficacy of human G-CSF) and examples (of pharmaceutical dosage forms) but it should be understood that the present invention is by no means limited to these examples.

REFERENTIAL EXAMPLE 1

Preparation of human G-CSF by cultivation of human G-CSF producing cells

G-CSF producing cell strain CHU-1 derived from human oral cancer cells was established by the method described in Example 1 provided in the specification of Japanese Patent Public Disclosure No. 61-227526. Similar cell strain CHU-2 (CNCM Accession Number I-483) was established by the same method. Each of these cell strains was suspended in a liquid culture RPMI 1640 containing bovine fetal serum, transferred into a roller bottle and whirl-cultured. When the cells grew to form a confluent layer on the inner surface of the roller bottle, the culture solution was replaced by a serum-free RPMI 1640. After 4-day culture, the supernatant of the culture was recovered and cultivation was continued with a serum-containing RPMI 1640 being added. After 3-day culture, the culture solution was again replaced by a serum-free RPMI 1640 and the supernatant of the culture was recovered 4 days later. By repeating these procedures, the supernatant of the culture was recovered. The so obtained serum-free supernatant of the culture was concentrated about 1,000 times by ultrafiltration and subsequently subjected to purification and assay by the same procedures as described in the examples provided in the specification of Japanese Public Disclosure No. 61-227526.

REFERENTIAL EXAMPLE 2

Preparation of human G-CSF by the recombinant gene technology

The following description applies to the preparation of +VSE or −VSE depending upon whether m=1 or 0 in the amino acid sequence described above.

A cDNA fragment harboring a human G-CSF gene that had been cut from Escherichia coli (E. coli) stain 1766 deposited by the assignee with the Fermentation Research Institute, the Agency of Science and Technology (FERM BP-955 for −VSE and FERM BP-954 for +VSE) was incorporated into a vector pkKCR to construct a plasmid pHGV2 (in the case of −VSE) or pHGG4 (in the case of +VSE). The plasmids were treated with SalI and subsequently reacted with a DNA polymerase Klenow fragment.

After attaching an EcoRI linker, this DNA was partially digested with EcoRI again and a fragemnt of ca. 2.7 kb was recovered by electrophoresis through an agarose gel.

In a separate step, a plasmid pAdD26SVpA [Kaufman, R. G. & Sharp, P. A. (1982) Mol. Cell. Biol., 2, 1304–1319] was treated with EcoRI and dephosphorylated by treatment with BAP. Subsequently, an EcoRI fragment of pAdD26SVpA was recovered by electrophoresis following treatment with phenol.

The 2.7 kb fragment and the pAdD26SVpA fragment thus obtained were annealed and used in transforming E. coli strain DHI by the rubidium chloride procedure to construct a plasmid pHGV2-dhfr (in the case of −VSE) or pHGG4-dhfr (in the case of +VSE).

CHO cells (dhfr− strain:courtesy of Dr. L. Chasin of Columbia University) were cultivated for growth in alpha-minimal essential medium containing 10% calf serum (α-MEN supplemented with adenosine, deoxyandensine and thymidine) in plates (9 cmφ, Nunc). The cultured cells were transformed by the calcium phosphate procedure [Wigler et al., Cell. 14, 725 (1978)] in the following manner.

A carrier DNA (calf thymus DNA) was added in an appropriate amount to 1 μg of the previously prepared plasmid pHGV2-dhfr (in the case of −VSE) or pHGG4-dhfr (+VSE) and the mixture was dissolved in 375 μl of a TE solution, followed by addition of 125 μl of 1 M $CaCl_2$. After the solution was cooled on ice for 3–5 minutes, 500 μl of 2 ×HBS (50 mM Hepes, 280 mM NaCl, and 1.5 mM phosphate buffer) was added to the solution. After recooling on ice, the solution was mixed with 1 ml of the culture of CHO cells, transferred onto plates, and incubated for 9 hours in a $CO_2$ incubator.

Following washing with TBS (Tris-buffered saline), addition of 20% glycerol-containing TBS, and re-washing, a non-selective medium (the α-MEN medium described above except that it was supplemented with nucleotides) was added. After 2-day incubation, a 10-fold dilution of the culture was transferred onto a selective medium (not supplemented with nucleotides). The cultivation was continued, with the medium being replaced by a fresh selected medium every 2 days, and the resulting colonies were selected and transferred onto fresh plates, where the cells grew in the presence of 0.02 μm methotexate (MTX), followed by cloning through growth in the presence of 0.1 μm MTX.

As a result of further cloning procedures, it was confirmed that human G-CSF had been produced in an amount of at least 10 mg/l (in the cases of −VSE) or at least 1 mg/l (in the case of +VSE).

Purification of human G-CSF and assaying of its activity were conducted by the procedures described in the examples provided in the specification of Japanese Patent Public Disclosure No. 62-236488.

EXPERIMENTAL EXAMPLE 1

G-CSF triggered enhancement of plasminogen activator (PA) production by bovine carotid arterial endothelial cells Vascular endothelial cells collected from bovine carotid artery were dispersed in Eagle's minimum essential medium containing 20% bovine fetal serum, 50 unit/ml of penicillin and 50 μg/ml of streptomycin and the first-generation cultivation was conducted in a Petri dish at 37° C. in a 95% air+5% $CO_2$ atmosphere. After a confluent layer formed on the bottom of the Petri dish, the cells were dispersed in a 0.05% trypsin solution and subcultured. In the next place, serial cultivation was conducted under the same conditions as in the first-generation cultivation except that the concentration of bovine fetal serum was changed to 10%. The resulting large volume of cells were cultivated for 2 days in a Petri dish using the already described Eagle's minimum essential medium containing 10% bovine fetal serum in the presence of the G-CSF prepared in Referential Example 2, with its concentration being varied from 0 to 300 ng/ml. Thereafter, the cells were washed with a medium containing neither G-CSF nor serum and further cultivated in a similar medium for 8 hours to prepare a conditioned medium. The activity of PA secreted in this conditioned medium was assayed by a coupled fluorometric method. In the first step, plasminogen was activated to plasmin by PA, and in the second step, the activity of the resulting plasmin was measured using t-butyloxycarbonyl-L-valyl-L-leucyl-lysine-4-methylcoumaryl-7-amide (BOC-Val-Leu-Lys-MCA) as a synthetic substrate. PA activity was expressed in terms of urokinase international unit (I.U.).

Figure 2:
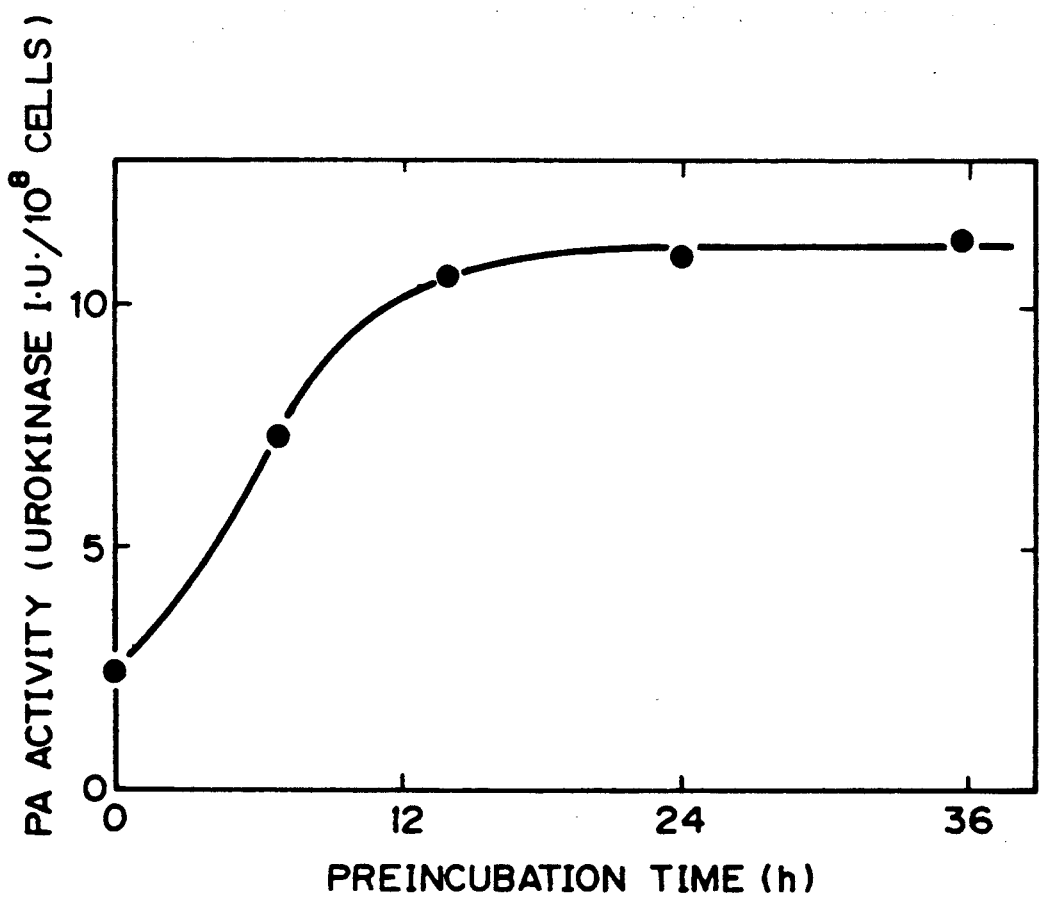
FIG. 2 is a graph showing the corelationship between the time of preincubation in the presence of human G-CSF and PA production by bovine endothelial cells.

As will be clear from FIG. 1, the PA activity increased dramatically with the increasing addition of G-CSF and reached a plateau at a concentration of 50 ng/ml. As FIG. 2 shows, PA production increased with the lapse of preincubation time and substantially reached a maximum in 12 hours. The activity increase was five times as great as that of the control group. These results show that G-CSF acts on vascular endothelial cells to promote their PA production by a marked degree.

In order to confirm that PA production increased not only extracellularly but also intracellularly, the following experiment was also conducted. After 2-day cultivation in the presence of G-CSF, the cells were washed and one half of them was homogenized with 0.5% Triton X-100 and the cellular extract obtained was assayed for its intracellular PA activity. The other half of the cells was cultivated for 8 hours in the manner already described and the resulting culture was assayed for the activity of extracellular PA secretion. The results are shown in Table 1 below, form which one can see that the intracellular activity of PA increased as much as the extracellular activity. When a protein synthesis inhibitor cyclohexamide was added to the medium during the 2-day cultivation, both intracellular and extracellular PA production was completely inhibited in the subsequent period of cultivation for 8 hours.

These facts show that the PA production by vascular endothelial cells was appreciably enhanced by adding G-CSF to the medium.

TABLE 1

Intracellular and Extracellular PA Activities of Endothelial Cells Treated with Human G-CSF

| Treatment | PA Activity (urokinase I.U./$10^8$ cells) | |
|---|---|---|
| | Extracellular supernatant | Intracellular |
| Control | 1.85 ± 0.45 | 2.59 ± 1.29 |
| G-CSF (50 ng/ml) | 9.09 ± 1.08 | 9.40 ± 3.30 |

EXPERIMENTAL EXAMPLE 2

Promotion of the fibrinolytic activity of vascular endothelial cells by G-CSF

A hundred microliters of thrombin (5 µ/ml) was added to 2.4 ml of a fibrinogen solution (13.5 mg/ml) in a culture dish and incubation was performed at 37° C. for 3 hours to form a fibrin gel. On the gel, bovine carotid arterial endothelial cells were grown in Eagle's minimum essential medium containing 10% bovine fetal serum, penicillin (50 µ/ml) and streptomycin (50 µg/ml) in the presence of 500 ng/ml of the G-CSF obtained in Referential Example 2. An untreated control group was also cultivated under the same conditions. After 43 hours of the cultivation, a small lysis zone was observed in the control group as shown in FIG. 3 and this reflects nominal secretion of PA from the cells in the control group. A larger and more distinct lysis zone was observed in the cells of the treated group. G-CSF stimulated these cells to synthesize and secrete more PA, with consequent activation of the plasminogen in the culture to produce plasmin which lysed the fibrin gel.

These results show that human G-CSF acts on vascular endothelial cells to promote PA synthesis and secretion, with the secreted PA activating the surrounding plasminogen to produce plasmin, which then lyses fibrin which is the major component of thrombus.

The foregoing data establishes that human G-CSF stimulates vascular endothelial cells to promote PA release, thereby enhancing the fibrinolytic activity of these cells.

EXPERIMENT EXAMPLE 3

Figure 4:
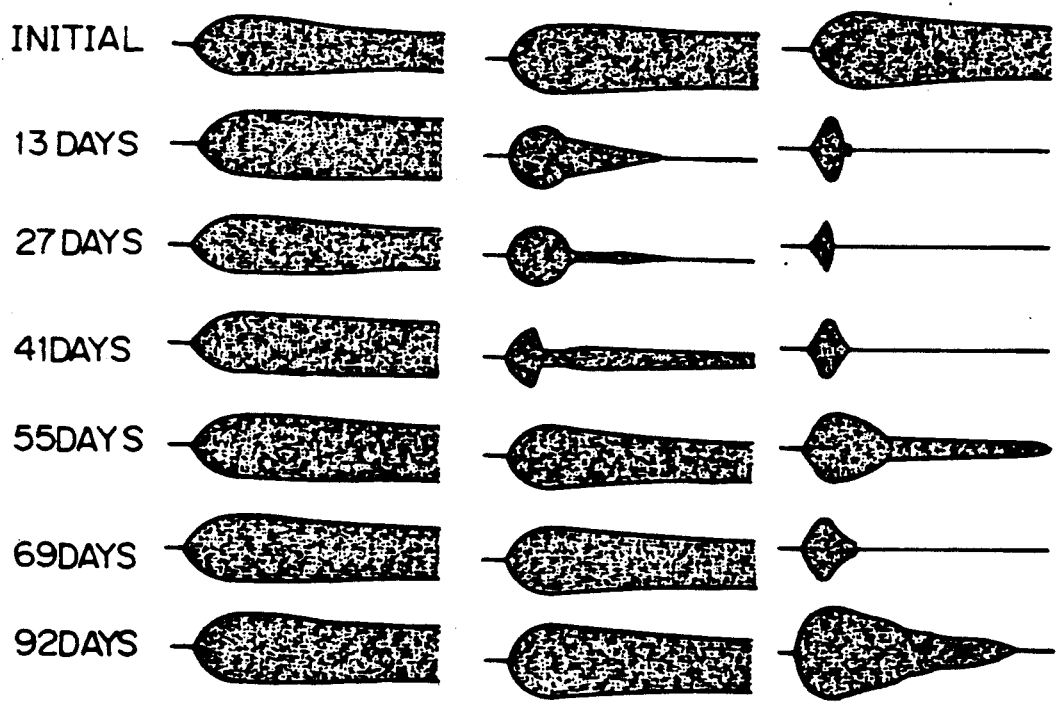
FIGS. 4A, 4B, 4C shows the time-dependent changes in the TEG pattern upon continued administration of human G-CSF to Rhesus monkey for 13 weeks.

Enhancement of the fibrinolytic activity of Rhesus monkey by contained administration of human G-CSF After human G-CSF was administered continuously to Rhesus monkey, a peripheral blood sample was taken and its fibronlytic activity was assayed with a thromboelastgraph (TEG) using a clot tracker Model TE-400 (Elmer). The result is shown in FIG. 4a, form which one can see that in the control group, the amplitude of a TEG pattern increased when coagulation started and the maximum amplitude (MA) of the pattern decreased gradually as fibrinolytic activity developed at a later time. In contrast, with the animals given subcutaneous injection of human G-CSF in an amount of 1 µg/kg, a marked enhancement of fibrinolytic activity occurred in the TEG pattern as early as 2 weeks after the injection (see FIG. 4b; also see Reference 1, "JISSEN SHIKETSU GYOKOGAKU", ed. by M. Fujimaki et al., pp. 189-191), revealing the decrease in the elasticity of coagulation clot and fibrin clot in the proceeds of blood coagulation. As FIG. 4c shows, the enhancement of fibrinolytic activity was more marked in the animals given continued administration of human G-CSF in an amount of 10 µg/kg [see Reference 2, "Analysis of Clot Tracer Patterns" in KISO TO RINSHO vol. 12, No. 6, June (1978), pp. 76-78]. As Reference 2 shows, when urokinase is added to a coagulated sample of normal human blood, lysis occurs to produce a single-lined pattern. A tendency which was entirely identical to this thromboelastogram was observed in almost all cases of human G-CSF administration.

The above results show that human G-CSF was capable of achieving not only in vitro but also in vivo enhancement of fibrinolytic activity. In summary:

(1) vascular endothelial cells preincubated in the presence of human G-CSF synthesized and secreted about 5 times as much PA as when they were preincubated in the absence of human G-CSF;

(2) when human G-CSF and vascular endothelial cells were cultured on a fibrin gel, the synthesis and secretion of PA by the endothelial cells were promoted, with subsequent activation of the concomitant plasminogen to plasmin, which lysed the gel of fibrin which is the major component of thrombus (i.e., human G-CSF stimulated the vascular endothelial cells to liberate PA, thereby producing enhanced fibrinolytic activity); and (3) analysis of a thromboelastogram of a peripheral blood sample taken from Rhesus monkey administered continuously with human G-CSF revealed enhancement of the fibrinolytic activity of the animal.

It was therefore established that human G-CSF is capable of achieving a marked enhancement of fibrinolytic activity both in vitro and in vivo.

EXAMPLE 1

Polysorbate 20 (Tween 20 ®:polyoxyethylenesorbitan monolaurate) which is a nonionic surfactant was added to a 50 µg/ml solution of the human G-CSF prepared and purified in Referential Example 1 in 10 mM phosphate buffer (pH 7) so that the concentration of Polysorbate 20 became 0.1 mg/ml. After adjusting the osmotic pressure to be the same as the of the physiological saline, the solution was filtered through a membrane filter having a pore size of 0.22 µm to remove microorganisms, and charged into vials which had been sterilized. The vials were covered with sterilized rubber closures and then sealed with aluminum caps to give a liquid preparation for injection. The vials were stored in the dark at a temperature of lower than 10° C.

EXAMPLE 2

Polysorbate 80 (Tween 80 ®:polyoxyethylenesorbitan monolaurate) which is a nonionic surfactant was added to a 100 µg/ml solution of the human G-CSF prepared and purified in Referential Example 2 in 10 mM phosphate buffer (pH 7) so that the concentration of Polysorbate 80 became 0.1 mg/ml. After adjusting the osmotic pressure to be the same as the of the physiological saline, the solution was filtered through a membrane filter having a pore size of 0.22 µm to remove microorganisms, and charged into vials which had been sterilized. The vials were covered with sterilized rubber closures and then sealed with aluminum caps to give a preparation for injection. The vials were stored in the dark at a temperature of lower than 10° C.

EXAMPLE 3

Polysorbate 20 (Tween 20 ®:polyoxyethylenesorbitan monolaurate) which is a nonionic surfactant, HSA and mannitol were added to a 50 μg/ml solution of the human G-CSF prepared and purified in Referential Example 1 in 10 mM phosphate buffer (pH 7) so that the concentrations of Polysorbate 20, HSA and mannitol became 0.1 mg/ml, 10 mg/ml and 50 mg/ml, respectively. The solution was filtered through a membrane filter having a pore size of 0.22 μm to remove microorganisms, and charged into vials which had been sterilized. The rubber closures are loosely fitted by the rubber insertion machine so that two gaps of the rubber closure are exposed to allow for the freeze-drying process, and the charged solution was freeze dried. The vials were then sealed with the rubber closures and then with aluminum caps to give a freeze-dried preparation for injection. The preparation in the vials which can be stored at room temperature is used after reconstituting it with distilled water for injection.

EXAMPLE 4

Polysorbate 80 (Tween 80 ®:polyoxyethylenesorbitan monolaurate) which is a nonionic surfactant, gelatin, and mannitol were added to a 100 μg/ml solution of the human G-CSF prepared and purified in Referential Example 2 in 10 mM phosphate buffer (pH 7) so that the concentrations of Polysorbate 80, gelation and mannitol became 0.1 mg/ml, 10 mg/ml and 50 mg/ml, respectively. The solution was filtered through a membrane filter having a pore size of 0.22 μm to remove microorganisms, and charged into vials which had been sterilized. The rubber closures are loosely fitted by the rubber insertion machine so that two gaps of the rubber closure are exposed to allow for the freeze-drying process, and the charged solution was freeze dried. The vials were then sealed with the rubber closures and then with aluminum caps to give a freeze-dried preparation for injection. The preparation in the vials which can be stored at room temperature is used after reconstituting with distilled water for injection.

The thrombus control agent of the present invention which contains human G-CSF as an effective ingredient potentiates the ability of human vascular endothelial cells to produce PA, which ability is inherent in the human body, thereby converting the plasminogen blood to its activated form (plasmin), which gives rise to fibrinolytic activity, with consequent dissolution of thrombi. Further, the number of neutrophiles increases as a result of G-CSF administration and they work in such a way as to promote the processing of lysed thrombi. These two actions combine to effectively dissolve and eliminate thrombi. Therefore, the present invention provides a useful thrombus control agent with reduced side effects.

What is claimed is:

1. A method for the dissolution of thrombi in a mammal which comprises:
    (a) providing a composition comprising purified human granulocyte colony stimulating factor (G-CSF) in a pharmaceutically-acceptable medium; and
    (b) administering the composition to the mammal:- wherein the G-CSF is present in the composition in an amount sufficient to increase the production of plasminogen activator activity in the blood so as to lyse fibrin and dissolve thrombi.

2. The method according to claim 1, wherein the composition is administered by injection.

3. The method according to claim 1 or claim 2, wherein the composition is administered such that 0.1 μg–1,000 μg of G-CSF is delivered to the mammal one to seven times per week.

4. The method according to claim 3, wherein the composition is administrated such that 0.1 μg–500 μg of G-CSF is delivered to the mammal one to seven times per week.

5. The method according to claim 1 or claim 2, wherein the composition is administrated in a dose of 1 μg–10 μg of G-CSF per kg of body weight.

6. The method according to claim 1, wherein the granulocyte colony stimulating factor is provided using recombinant gene technology.

7. A method for increasing fibrinolytic activity in blood which comprises:
    (a) providing a composition comprising purified human granulocyte colony stimulating factor (G-CSF) in a pharmaceutically-acceptable medium; and
    (b) administering the composition to the mammal:- wherein the G-CSF is present in the composition in an amount sufficient to increase the production of plasminogen activator activity in the blood, thereby increasing fibrinolytic activity.

8. The method according to claim 7 for control of venous and arterial thrombi by increasing fibrinolytic activity:wherein the composition comprises about 50–100 μg/ml of human granulocyte colony stimulating factor in 10 mM phosphate buffer and about 0.1 mg/ml of a pharmaceutically acceptable nonionic surfactant-:and wherein G-CSF enhances the production of plasminogen activator which is capable of activating the fibrinolytic system.

9. The method according to claim 8 wherein the nonionic surfactant is selected from the group consisting of polyoxyethylenesorbitan monolaurate and polyoxyethylenesorbitan monooleate.

10. The method according to claim 8 which further comprises about 10 mg/ml of human serum albumin and about 50 mg/ml of mannitol.

11. The method according to claim 8 which further comprises about 10 mg/ml of gelatin and about 50 mg/ml of mannitol.

12. A method of increasing plasminogen activator activity in a mammal for dissolution of venous and arterial thrombi, comprising administering to the mammal a composition of purified human granulocyte colony stimulating factor (G-CSF) in a pharmaceutically-acceptable medium; wherein the G-CSF in the composition is present in an amount sufficient to promote increased production of plasminogen activator activity to dissolve thrombi.

13. The method according to claim 12, wherein the composition is administered by injection.

14. The method according to claim 12 or claim 13, wherein the composition is administered such that 0.1 μg–1,000 μg of G-CSF is delivered to the mammal one to seven times per week.

15. The method according to claim 14, wherein the composition is administrated such that 0.1 μg–500 μg of G-CSF is delivered to the mammal one to seven times per week.

16. The method according to claim 12 or claim 13, wherein the composition is administrated in a dose of 1 μg–10 μg of G-CSF per kg of body weight.

17. The method according to claim 12, wherein the granulocyte colony stimulating factor is provided using recombinant gene technology.

* * * * *

UNITED STATES PATENT AND TRADEMARK OFFICE
CERTIFICATE OF CORRECTION

PATENT NO.  : 5,202,117
DATED       : April 13, 1993
INVENTOR(S) : Koichiro Tsuji and Masayoshi Ono It is certified that error appears in the above-indentified patent and that said Letters Patent is hereby corrected as shown below:

| | |
|---|---|
| Column 1, line 65 | "mush" should be "much" |
| Column 2, line 61 | "is" the transformant should be "in" the transformant |
| Column 3, line 57 | "nitrogen" should be "mitogen" |
| Column 4, line 18 | "formation" should be "formulation" |
| Column 5, line 20 | "pkKCR" should be "pdKCR" |
| Column 6, line 2 | "$\mu$m" should be "$\mu$M" |
| Column 6, line 3 | "$\mu$m" should be "$\mu$M" |
| Column 7, line 55 | "contained" should be "continued" |

Signed and Sealed this

Eighth Day of March, 1994

Attest:

BRUCE LEHMAN

Attesting Officer   Commissioner of Patents and Trademarks